US00PP20282P2

(12) United States Plant Patent
van Dijk

(10) Patent No.: US PP20,282 P2
(45) Date of Patent: Sep. 8, 2009

(54) ***ANTHURIUM* PLANT NAMED 'ANTHABUDON'**

(50) Latin Name: ***Anthurium andreanum* L.**
Varietal Denomination: Anthabudon

(75) Inventor: Jan van Dijk, Bleiswijk (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 12/157,534

(22) Filed: Jun. 11, 2008

(51) Int. Cl.
*A01H 5/00* (2006.01)

(52) U.S. Cl. ..... Plt./369

(58) Field of Classification Search ..... Plt./369, Plt./365

See application file for complete search history.

*Primary Examiner*—Annette H Para
*Assistant Examiner*—Louanne C Krawczewicz Myers
(74) *Attorney, Agent, or Firm*—Jondle & Associates, P.C.

(57) ABSTRACT

A new *Anthurium* plant particularly distinguished by having bright-red, durable spathes that slowly turn brown-red with age, green, durable leaves, a long erect peduncle, rich shoot formation, flowers early and continuously throughout the year, an erect and full plant habit and a plant height of 45 cm to 55 cm, is disclosed.

2 Drawing Sheets

Genus and species: *Anthurium andreanum* L.
Variety denomination: 'Anthabudon'.

BACKGROUND OF THE NEW PLANT

The present invention comprises a new and distinct cultivar of *Anthurium,* botanically known as *Anthurium andreanum* L., and hereinafter referred to by the cultivar name 'Anthabudon'. The new cultivar originated from a hybridization made in 2000 in Bleiswijk, The Netherlands. The female parent was a red *Anthurium* pot plant 'Anthepedi' (U.S. Plant Pat. No. 18,644), while the male parent was a red *Anthurium* pot plant '99-2874-01' (unpatented).

The new cultivar was selected in 2002 from a selection of the hybridization and has been asexually reproduced repeatedly by tissue culture in Bleiswijk, The Netherlands over a five-year period. The present invention has been found to retain its distinctive characteristics through successive asexual propagations.

Plant Breeder's Rights for this cultivar were applied with the European Union on Jan. 26, 2007. 'Anthabudon' has not been made publicly available more than one year prior to the filing of this application.

SUMMARY OF THE INVENTION

The following are the most outstanding and distinguishing characteristics of this new cultivar when grown under normal horticultural practices in Bleiswijk, The Netherlands.

1) Bright-red, durable spathes with a typical undulated surface;
2) Green leaves that are big and durable;
3) Long, erect peduncle which holds the inflorescence well above the foliage;
4) Rich shoot formation;
5) Erect and full plant habit;
6) Flowers early and continuously throughout the year; and
7) Is a pot plant, with a plant height of 45 cm to 55 cm.

DESCRIPTION OF THE PHOTOGRAPHS

This new *Anthurium* plant is illustrated by the accompanying photographs which show the overall plant habit including blooms, buds and foliage of the plant; the colors shown are as true as can be reasonably obtained by conventional photographic procedures. The photographs are of a 48-week old plant grown in a greenhouse in Bleiswijk, The Netherlands in 2007.

DESCRIPTION OF THE NEW CULTIVAR

Figure 1:
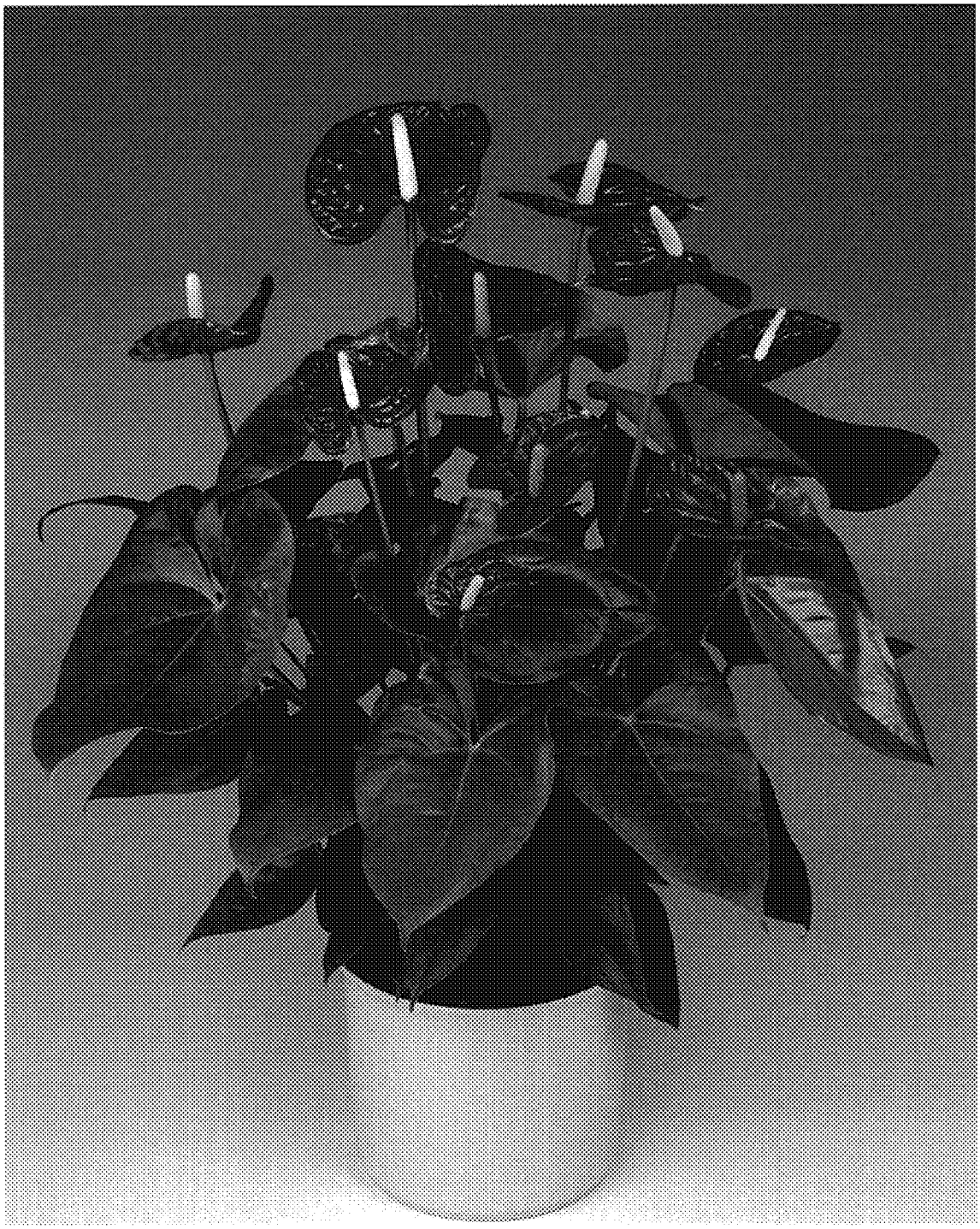
FIG. 1 shows the overall plant habit, including blooms, buds and foliage.
Figure 2:
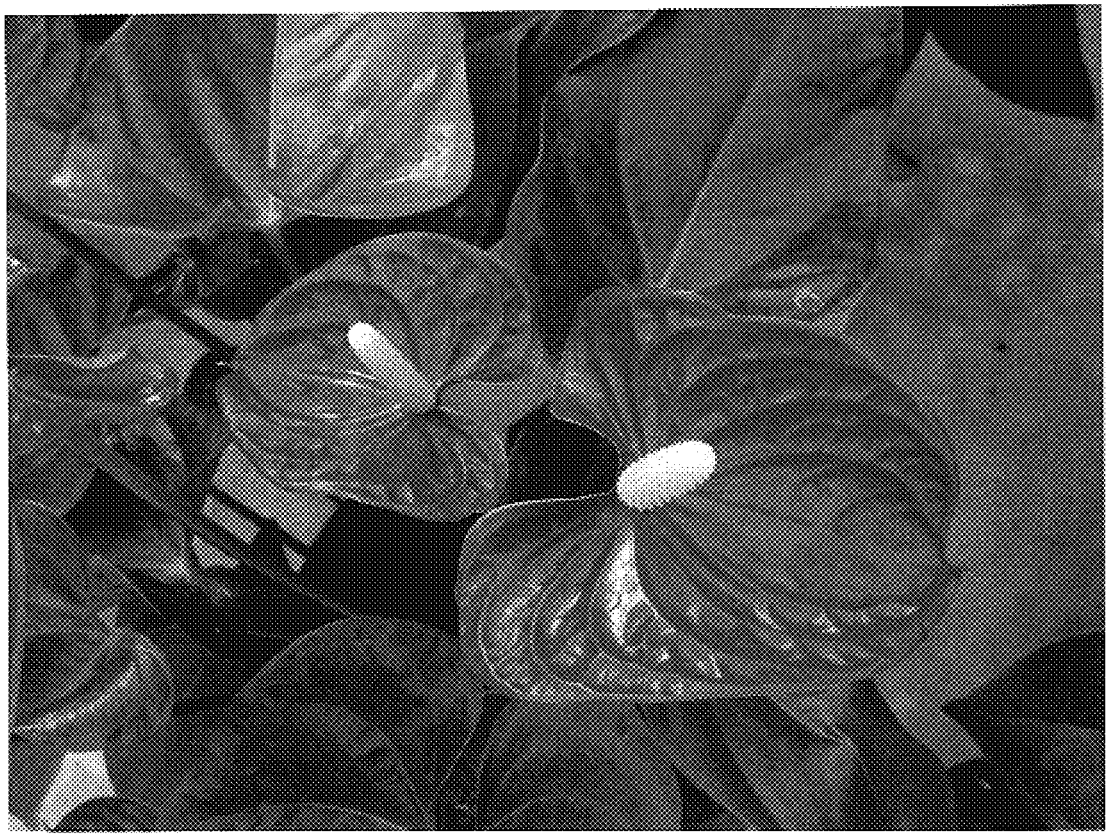
FIG. 2 shows the mature spathe.

The following detailed description sets forth the distinctive characteristics of 'Anthabudon'. The data which define these characteristics were collected from asexual reproductions carried out in Bleiswijk, The Netherlands. The plant history was taken on 48-week old plants which were planted from tissue culture in 17-cm pots and grown in a glass greenhouse between 19° C. and 24° C. Observations were made in November of 2007. Color readings were taken under 5000 lux natural light in the greenhouse. Color references are primarily to the R.H.S. Colour Chart of The Royal Horticultural Society of London (R.H.S.) (2001).

DETAILED BOTANICAL DESCRIPTION

Classification:
*Family.*—Araceae.
*Botanical.*—*Anthurium andreanum* L.
*Common name.*—*Anthurium.*
*Cultivar name.*—'Anthabudon'.

Parentage:
*Female parent.*—'Anthepedi', a red-flowered *Anthurium* plant (U.S. Plant Pat. No. 18,644).
*Male parent.*—'99-2874-01', a red-flowered *Anthurium* plant (unpatented).

Propagation:
*Propagation.*—Tissue culture.
*Root description.*—Fleshy-pink to cream roots with smaller hairy lateral roots; root-tips are yellow.
*Time to produce a finished flowering plant.*—45 to 50 weeks for a 17 cm pot.

Plant:
*Growth habit.*—Herbaceous perennial.
*Height (measured from soil, including inflorescence).*—45 cm to 55 cm.
*Width (measured from leaf tips).*—40 cm to 45 cm.

Leaves:
*Immature leaves.*—Length: 11 cm to 15 cm. Width: 8 cm to 10 cm. Color: Upper surface: RHS 137A (Green). Lower surface: RHS 137B. Texture (both upper and lower surfaces): Very shiny.
*Mature leaves.*—Length (fully expanded): 23 cm to 25 cm. Width: 13 cm to 15 cm. Shape: Elliptical-cordate, weakly cupped. Apex: Acuminate. Base: Cordate. Leaf blade angle with the petiole: Between 110 degrees and 130 degrees. Leaf margin: Entire. Color: Upper surface: RHS 139A (green). Lower surface: RHS 146A (light-green). Texture (both upper and lower surfaces): Shiny, leathery and thick; weakly undulated.
*Venation.*—Pinnate veining; the mid-vein and primary veins (the veins which radiate out from junction of petiole and leaf) protrude at the underside of the leaf blade.
*Venation color.*—Upper surface: RHS 137C (green). Lower surface: RHS 145A (light green).
*Lobes/wings.*—Arrangement: Leaf blade has two big lobes extending past the petiole. Length of lobes of mature leaf blades: 5 cm to 6.5 cm. Width of lobes of mature leaf blades: 5 cm to 6.5 cm. Distance for petiole/leaf junction to highest point on lobes of mature leaf blades: 5 cm to 6.5 cm. Color lobe/wing upper surface: RHS 139A. Color lobe/wing lower surface: RHS 146A.
*Petiole.*—Cross-section: Round. Diameter: 0.4 cm to 0.6 cm. Length: 20 cm to 25 cm for a mature leaf size. Color: Mature leaf: RHS 146B. Immature leaf: RHS 146B. Cataphyl color surrounding the petiole: Outside: RHS 184A (purple-red). Inside: RHS 184C (purple). Geniculum (A small "knee-like" structure or joint below the leaf blade that connects the leaf blade to the peduncle and only very slightly distinguishable from the petiole.): Length is 2.0 cm to 2.5 cm, Width is 0.4 cm to 0.6 cm, Color is RHS 146B.

Inflorescence:
*Arrangement.*—Single.
*Flowering habit (length of flowering season).*—Continuous.
*Number of inflorescences per plant.*—8 to 10.
*Fragrance.*—Absent.
*Inflorescence longevity on the plant.*—Over one year.
*Inflorescence longevity as a cut flower.*—Approximately 40 days.

Spathe:
*Buds.*—The spathe is tightly rolled around the spadix and extrudes from the peduncle sheath. After the spathe is fully opened the peduncle elongates some extra centimeters.
*Arrangement.*—Spathe angle with the peduncle is between 90 degrees and 110 degrees; the spathe stands on a slightly curved wiry peduncle about 8 cm to 10 cm above the foliage.
*Shape.*—Oblong-cordate with a typical undulated surface.
*Apex.*—Mucronate tip.
*Base.*—Cordate.
*Margin.*—Smooth (entire).
*Texture.*—Blistered.
*Size.*—Height: 32 cm to 38 cm (Peduncle length). Length: 10 cm to 12 cm. Width: 10 cm to 12 cm.
*Color.*—Just fully open: Upper surface: RHS 45A (bright-red). Lower surface: RHS 47A (pink-red). 7 to 8 weeks after opening: RHS 45A and in the lobes at the base RHS 185A (brown-purple). 14 to 16 weeks after opening: The whole spathe most resembles RHS 185A (brown-purple).

Peduncle:
*Shape.*—Erect.
*Cross-section.*—Round.
*Length.*—32 cm to 38 cm.
*Diameter.*—0.5 cm to 0.7 cm.
*Color.*—RHS 146D at unrolling of spathe, slowly turning RHS 166A (brown) when the spathe matures.

Flowering time:
*General.*—One small rooted untreated tissue culture plant of 2 cm tall will flower, depending on season, after 9 to 10 months and 2 to 3 blossoms appear. More blossoms appear after some additional weeks so that a full flowering and commercial plant will have 8 to 10 bright red spathes. Smaller blossoms may occur on less mature growth.

Spadix:
*Size.*—Length: 4 cm to 6 cm (depending on flower size). Width (at apex): 0.8 cm to 0.9 cm. Width (at base): 1.0 cm to 1.2 cm.
*Shape.*—Columnar.
*Apex.*—Rounded.
*Base.*—Truncate.
*Margin.*—Entire.
*Color.*—Immature: RHS 21A (yellow). Mature: RHS 158C (white). Ages to: RHS 137A (green).

Flowers:
*Quantity per spadix.*—250 to 300.
*Spadix flower arrangement.*—Bisexual, rounded in cross-section.
*Shape.*—Rounded.
*Size.*—Length: 0.1 cm to 0.2 cm. Diameter (maximum): 0.2 cm.
*Color.*—RHS 155B (white).

Reproductive organs:
*Stamens.*—Not visible.
*Pollen.*—Abundant.
*Pollen color.*—RHS 156D (white).
*Pistil.*—Quantity: Many. Length: Less than 0.01 cm. Color: RHS 156D.
*Style.*—Not observed.
*Stigma.*—Shape: Ovoid. Diameter: Less than 0.01 cm. Color: RHS 155D (white).
*Ovary.*—Rarely visible.
*Ovary color.*—RHS155D (white).

Fruit and seed set: Seed production has not been observed to date.

Disease and insect resistance: No particular resistance or susceptibility that is different from other *Anthurium* varieties.

COMPARISON WITH PARENTAL AND COMMERCIAL CULTIVARS

'Anthabudon' differs from the female parent and commercial variety 'Anthepedi' (U.S. Plant Pat. No. 18,644), by having bigger leaves and a more erect plant habit, while 'Anthepedi' is more compact with smaller leaves. See Table 1 below.

'Anthabudon' differs from the male parent '99-2874-01' (unpatented), by having a smaller spathe and a shorter spadix.

TABLE 1

| Comparison of characteristics between 'Anthabudon' and 'Anthepedi' | | |
|---|---|---|
| Characteristic | 'Anthabudon' | 'Anthepedi' |
| Leaf length | 23 cm to 25 cm | 17 cm to 20 cm |
| Leaf width | 13 cm to 15 cm | 11 cm to 13 cm |

TABLE 1-continued

| Comparison of characteristics between 'Anthabudon' and 'Anthepedi' | | |
|---|---|---|
| Characteristic | 'Anthabudon' | 'Anthepedi' |
| Cataphyl color (surrounding petiole) | RHS 184A (Purple-red) | RHS 144B (Light-green) |
| Spadix length | 4 cm to 6 cm | 4 cm |
| Peduncle length | 32 cm to 38 cm | 20 cm to 25 cm |

I claim:

1. A new and distinct cultivar of *Anthurium* plant, named 'Anthabudon', as shown and described herein.

* * * * *